(12) United States Patent
Parker et al.

(10) Patent No.: US 6,387,134 B1
(45) Date of Patent: May 14, 2002

(54) PROSTHETIC FOOT

(75) Inventors: James E. Parker; Peter R. Read, both of Hants (GB)

(73) Assignee: Vessa Limited, Hants (GB)

( * ) Notice: Subject to any disclaimer, the term of this patent is extended or adjusted under 35 U.S.C. 154(b) by 0 days.

(21) Appl. No.: 09/539,656

(22) Filed: Mar. 30, 2000

(30) Foreign Application Priority Data

Apr. 16, 1999 (GB) ............................................. 9908819

(51) Int. Cl.⁷ .................................................. A61F 2/66
(52) U.S. Cl. ...................................................... 623/55
(58) Field of Search ......................... 623/55, 53, 50, 623/52, 49, 54

(56) References Cited

U.S. PATENT DOCUMENTS

| | | | | |
|---|---|---|---|---|
| 2,357,893 A | * | 9/1944 | Harrington | 623/49 |
| 4,892,553 A | * | 1/1990 | Prahl | 623/55 |
| 5,019,109 A | | 5/1991 | Voisin | 623/49 |
| 5,066,305 A | * | 11/1991 | Firth | 623/66 |
| 5,507,838 A | * | 4/1996 | Chen | 623/55 |
| 5,701,686 A | | 12/1997 | Herr et al. | 36/27 |
| 5,769,896 A | * | 6/1998 | Rosendahl et al. | 623/49 |
| 6,206,934 B1 | * | 3/2001 | Phillips | 623/53 |

FOREIGN PATENT DOCUMENTS

| | | |
|---|---|---|
| EP | 331468 A2 | 9/1989 |
| GB | 625 528 | 6/1949 |
| GB | 2187102 B | 1/1990 |
| GB | 2311466 A | 10/1997 |
| WO | WO96/23461 | 8/1996 |
| WO | WO98/53769 | 12/1998 |

* cited by examiner

*Primary Examiner*—Bruce Snow
(74) *Attorney, Agent, or Firm*—Thomas Schneck (57) ABSTRACT

A prosthetic foot having a spring assembly with an anterior and posterior component, a snubber for limiting the movement of the spring assembly during assembly, and anterior and posterior shock absorbers provided between the components of the spring assembly and snubber. The arrangement of the posterior shock absorber, the spring assembly, and the snubber is such that ambulation results in the generation of a compressive force in the posterior shock absorber during a heel-strike phase and tensile force in the posterior shock absorber during a toe-off phase.

13 Claims, 7 Drawing Sheets

PROSTHETIC FOOT

FIELD OF THE INVENTION

This invention relates to prosthetic feet, and to prosthetic limbs employing those feet.

BACKGROUND OF THE INVENTION

As is well known in the art, an individual's or an amputee's gait during ambulation or other movement has several discrete phases, of which three are particularly significant. The first phase, known as heel strike, occurs when the heel contacts the surface along which the individual is moving. The second phase, known as flat foot, occurs when the foot is roughly parallel to the surface; and the third phase, known as toe-off, occurs when the heel of the foot is lifted from the surface and only the toe portion of the foot bears upon the surface to propel the individual forward.

Figure 1:
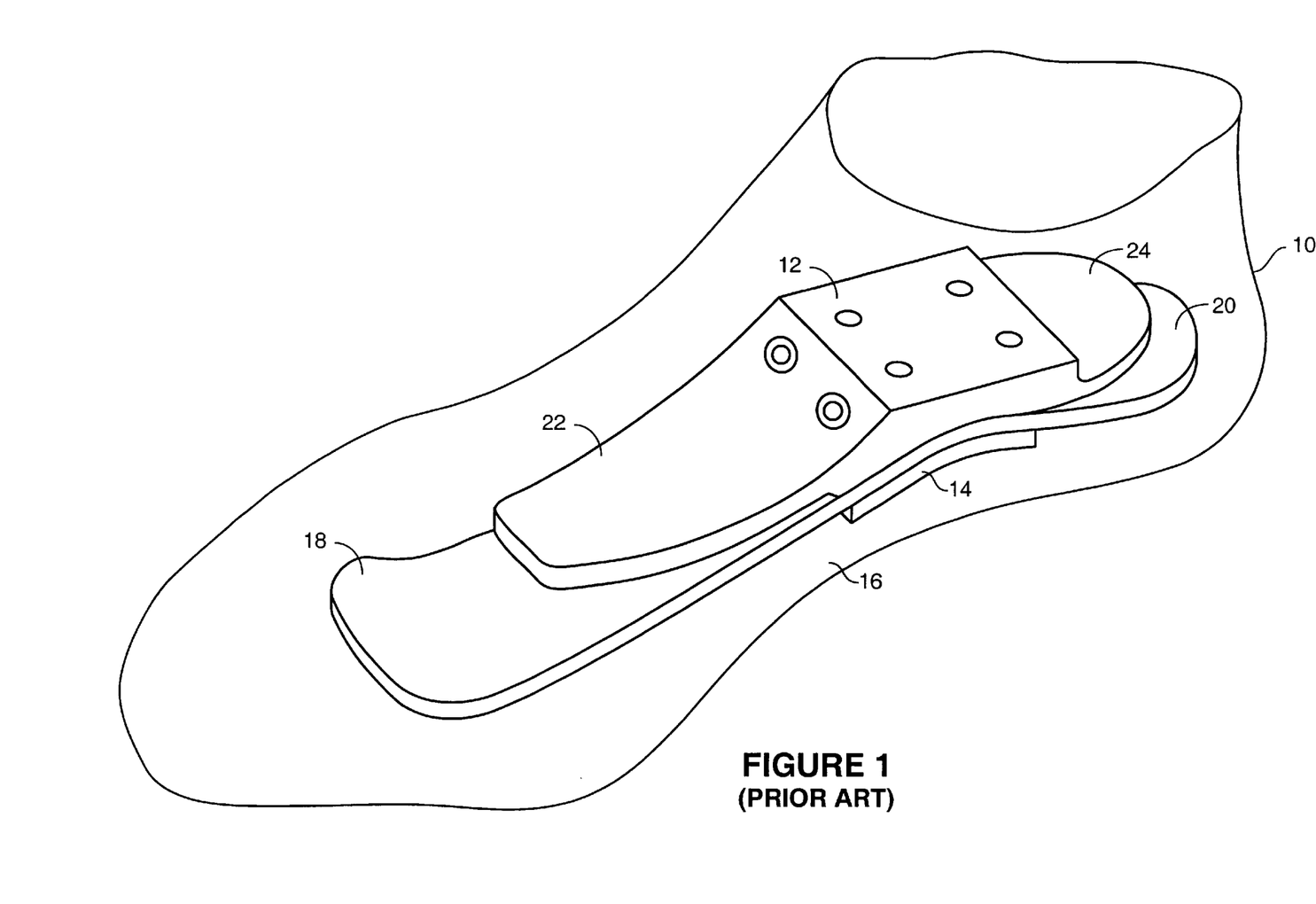
FIG. 1 is a cross-sectional view of a previously proposed prosthetic foot.

A variety of different types of prosthetic feet have previously been proposed. One of the earlier examples of a previously proposed foot is shown in FIG. 1 and described in detail in United Kingdom Patent No. 2187102. As shown in FIG. 1, the foot 10 comprises a keel 12 that is fixedly attached to a plate 14 joined to the cosmesis 16 of the foot. A spring member 18, 20 is sandwiched between the keel 12 and the mounting plate 14. The keel 12 is provided with cantilevered snubber arms 22, 24 that serve to limit deflection of the spring member during ambulation. The spring arms serve to absorb energy on heel strike, and to release that energy (or at least a proportion thereof) on toe-off to facilitate ambulation of the amputee.

Whilst the arrangement shown in FIG. 1 provides many advantages over older systems, it has subsequently been noted that the device can cause discomfort to some amputees in certain circumstances. For example, it has been noted that the co-operating spring member 18 and snubber arm 22 can cause jarring on heel strike. It has also been noted that a significant amount of the energy stored during heel strike is lost, and thus that less stored energy is available to aid the amputee during toe-off.

United Kingdom Patent Application No. 2311466 discloses one system that purports to alleviate these and other problems. The device disclosed in the publication employs a compressible energy storage device which can take the form of an elastomeric or rubber buffer or a gas-filled strut, for example. The device employs a heel spring and a toe spring that are each pivotally mounted to a frame within which the energy storage means is provided. A complicated locking arrangement is provided to lock the energy storage means in a compressed state when it has been compressed during heel strike, and to release the energy storage means from that locked compressed state during toe-off. This arrangement, whilst going some way to providing better energy recovery during ambulation, suffers from the disadvantages that it is unduly complicated, potentially noisy and, by virtue of its complicated construction, possibly prone to mechanical failure.

Another system that purports to aid energy recovery is disclosed in International Patent Publication No. WO98/53769. This publication discloses a device comprising an ankle member to which a heel member is pivotally attached, and a toe member pivotally attached to the heel member. The heel member includes an arm that extends beyond the pivot point between the ankle member and the toe member. Rubber buffers are provided between the heel member and the ankle member, between the heel member arm and the ankle member, and between the heel member arm and the toe member. Ambulation of the amputee causes compression of the various buffers and toe-off is assisted as these buffers decompress. The publication discloses a variety of different buffers that can serve to reduce the operating noise of the prosthesis.

Whilst this arrangement is advantageous over that disclosed in United Kingdom Patent Application No. 2311466, it still demonstrates a significant energy loss during ambulation. Furthermore, it has also been noted that problems can arise with rapid degradation of the buffers particularly when employed in prostheses fitted to amputees of over 90 kg in weight. These problems are exacerbated by the fact that the prosthesis can become significantly warmer during use, the increase in temperature causing a corresponding increase in the rate of buffer decay.

SUMMARY OF THE INVENTION

Aspects of the present invention variously seek to further improve energy recovery during ambulation, and to avoid problems associated with the use of the prosthesis by heavier amputees (i.e. by amputees of over 90 kg in weight). It will be understood, of course, that the prosthesis of the present invention can also provide significant advantages to amputees of less that 90 kg in weight.

In accordance with an aspect of the invention, there is provided a prosthetic foot comprising: a spring assembly having an anterior component and a posterior component; a snubber pivotally connected to said spring assembly for limiting movement of said spring assembly during ambulation; and anterior and posterior shock absorbers provided between respective components of said spring assembly and said snubber; wherein the arrangement of said posterior shock absorber, said spring assembly and said snubber is such that ambulation results in the generation of a compressive force in said posterior shock absorber during a heel strike phase and a tensile force in said posterior shock absorber during a toe-off phase. It should be noted that provision of an anterior shock absorber is optional.

This arrangement is advantageous as it allows energy recovery from the posterior shock absorber to occur both in the heel strike and toe-off phases thereby increasing the quantity of energy that can be recovered during toe-off.

Preferably, the anterior shock absorber is replaceable, or removable from said prosthesis for replacement. Preferably, the posterior shock absorber is replaceable, or removable from said prosthesis fore replacement. Preferably, the posterior shock absorber is releasably attached to said spring assembly and said snubber.

Preferably, the spring assembly comprises a pair of resiliently flexible members each of which have a pair of cantilevered arms. One of the pair of flexible members may be shorter than the other. The flexible members are preferably releasably attached to a keel that forms the remainder of said spring assembly.

Alternatively, the spring assembly may comprise a secondary resiliently flexible member fixedly attached to a keel, and one or more resiliently flexible sole members attached to said secondary flexible member, said keel being pivotally attached to said snubber.

A further aspect of the invention provides a prosthetic foot wherein at least one of said anterior and posterior shock absorbers are of a multi-layer construction.

Preferably, at least one of said anterior and posterior shock absorbers are of a multi-layer construction comprising a sandwich of compressible and substantially non-compressible or rigid layers.

Preferably, said posterior shock absorber is less compressible than said anterior shock absorber.

A further aspect of the invention provides a shock absorber for a prosthetic foot, said shock absorber having a multi-layer construction comprising a sandwich of compressible or resiliently deformable layers and substantially non-compressible or rigid layers.

Preferably the compressible or resiliently deformable layers have a hardness in the region of 65 IHRD or 75 IHRD.

A further aspect of the invention provides, in combination, a prosthetic foot as described herein, a shock absorber as described herein as said anterior shock absorber, and a shock absorber as described herein as said posterior shock absorber. A further aspect of the invention provides a prosthetic leg comprising an exoskeleton and a prosthetic foot as described herein. A further aspect of the invention provides a prosthetic leg comprising an endoskeleton and a prosthetic foot as described herein. A further aspect of the invention provides a cosmesis for a prosthetic foot as described herein, said cosmesis comprising strengthening means in the vicinity of a toe region thereof. Preferably, the strengthening means comprises a member embedded in the sole of the cosmesis. The strengthening means may comprise a strip of material of greater stiffness than the remainder of the cosmesis.

DESCRIPTION OF THE DRAWINGS

An embodiment of the invention will now be described, by way of example only, with reference to the accompanying drawings, in which.

DESCRIPTION OF PREFERRED EMBODIMENTS

Figure 7:
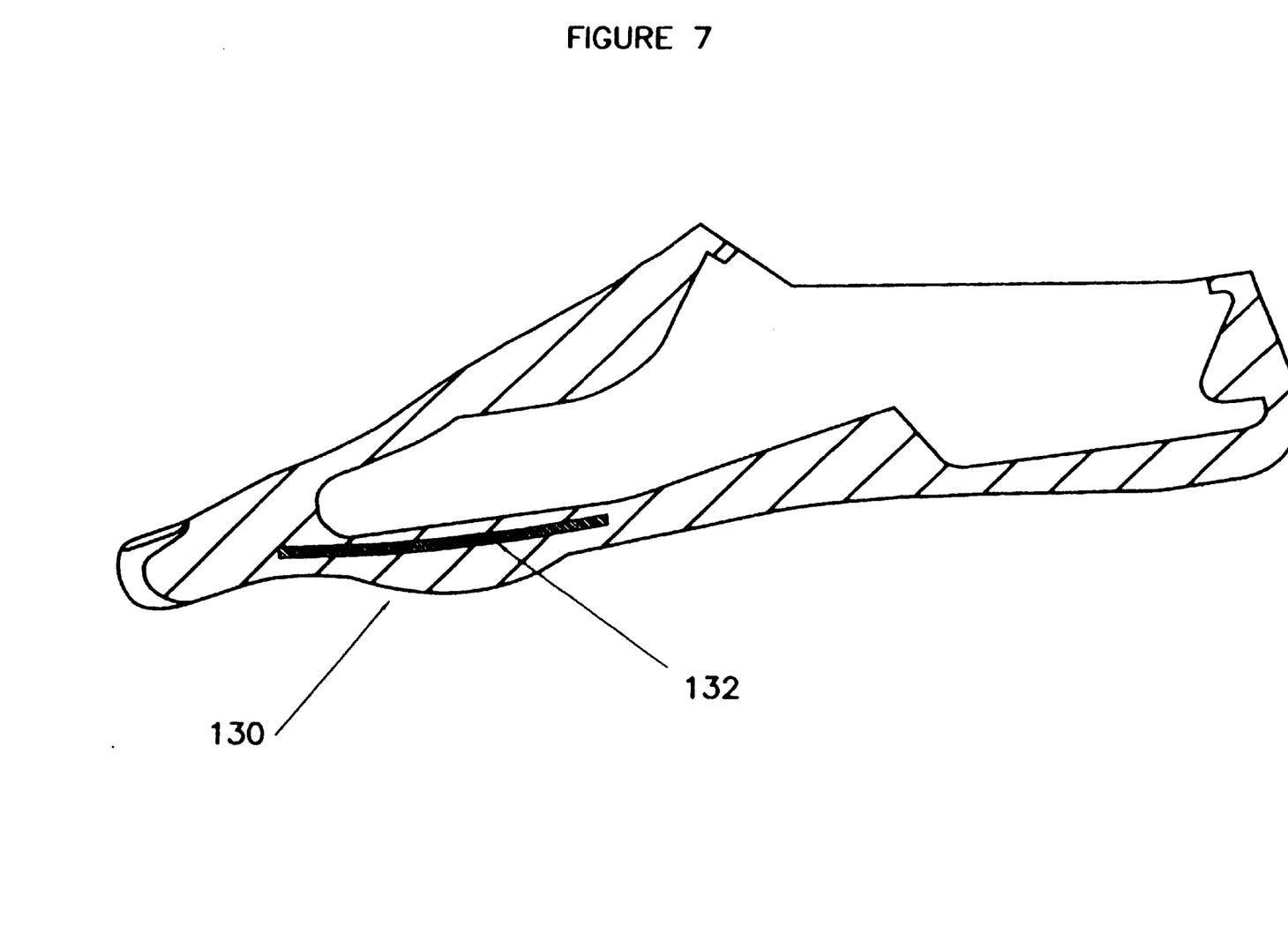
FIG. 7 is a cross-sectional view of a cosmesis.

As mentioned above, FIG. 2 shows an elevation of a prosthetic foot 40 according to an embodiment of the invention. For ease of illustration, the foot 40 is shown without a cosmesis, but it will be understood that a cosmesis will be fitted over the foot before use. FIG. 7 shows one such cosmesis, the construction of which will be later described.

Figure 2:
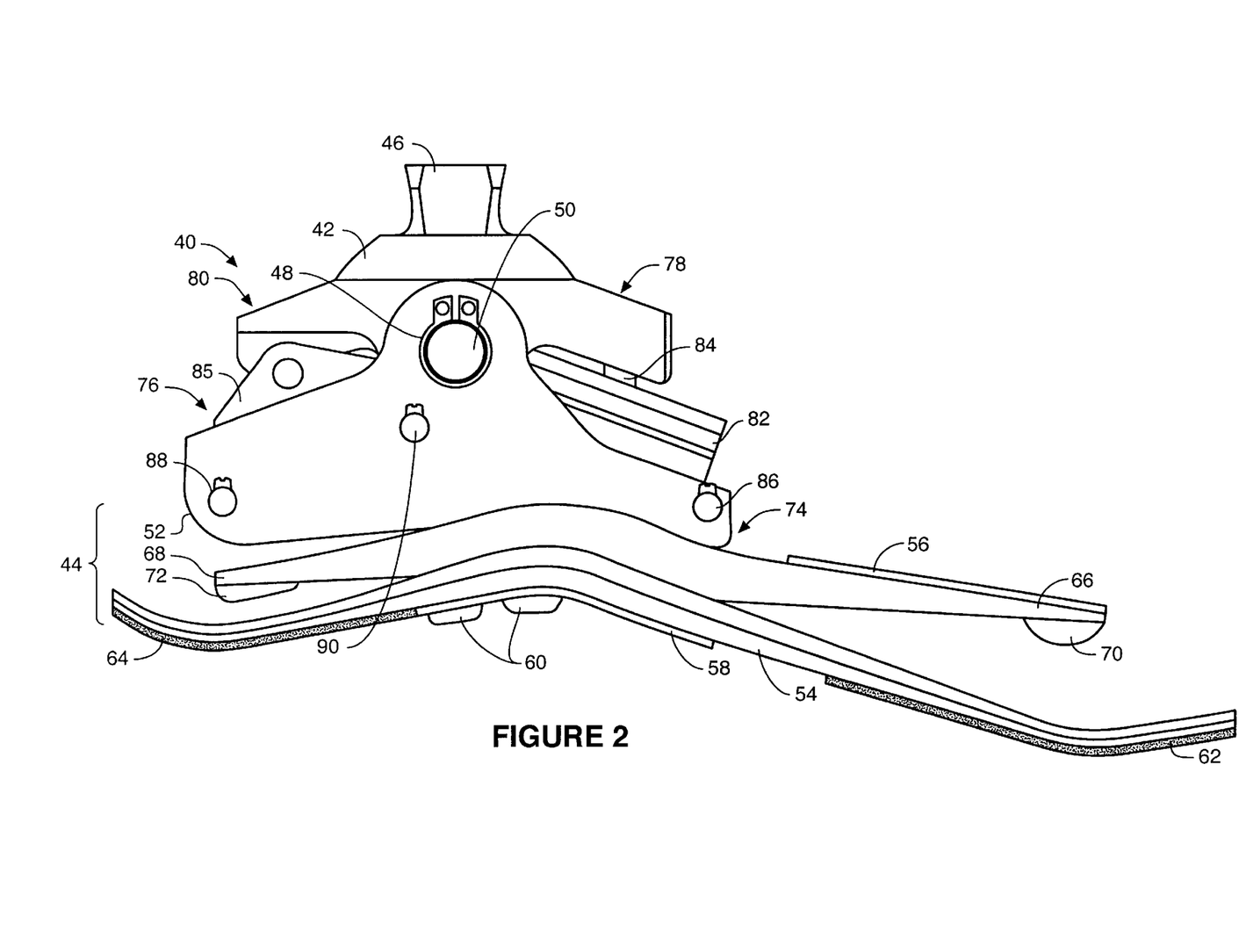
FIG. 2 is an elevation of a prosthetic foot according to an embodiment of the invention.

As shown, the foot 40 comprises a snubber 42 and a spring assembly 44. The snubber 42 is preferably generally triangular in shape (to reduce the weight of the snubber) and is provided with connecting means 46 by means of which the foot may be connected to a prosthetic limb. Many different connectors are commonly available and the snubber 42 may be modified in shape to accommodate whichever connector is appropriate.

The snubber 42 is provided with a bore that is alignable with a similar bore 48 in a component of the spring assembly 44, and through which an axle pin 50 is inserted. The axle 50 allows the spring assembly 44 to pivot through a predetermined extent controlled by the snubber in a manner to be later described.

The spring assembly 44 comprises a keel 52 and, in this embodiment, a sole spring arm 54 and a secondary spring arm 56. As shown in FIG. 1, it is known to provide a single sole spring arm but problems have been experienced with delamination of the composite arm material, as a result of which it has been proposed to provide a pair of sole spring arms each of which may be of a composite material or a metallic material. Whilst the preferred embodiment to be described employs a single sole spring arm 54 it should be noted that a pair of sole spring arms (or more than a pair of sole spring arms) could be provided instead should one wish to.

The spring arms 54, 56 are securely sandwiched between a mounting plate 58 and the underside of the keel 52 by fixing means 60 (which are screws in this particular case). The mounting plate 58 is preferably of metal and preferably the cosmesis (not shown) is formed around the mounting plate at the instep region thereof.

The sole spring arm 54 forms the sole of the prosthetic foot and is provided with cantilevered toe and heel arms 62, 64. The secondary spring arm 56 is also formed with cantilevered toe and heel arms 66, 68 of lesser extent than those of the sole spring arm 54. Toe and heel buffers 70, 72 are fixed to the underside of the toe and heel arms 66, 68 to cushion abutment of corresponding portions of the secondary 56 and sole 54 spring arms during ambulation.

The keel 52 is generally U-shaped in lateral cross-section and has an anterior portion 74 and a posterior portion 76. The snubber 42 is generally triangular and also comprises an anterior portion 78 and a posterior portion 80. An anterior shock absorber 82 is provided between the anterior portion 78 of the snubber 42 and the anterior portion 74 of the keel 52. The anterior shock absorber 82 is retained in place by a grub screw 84 in the snubber 42 and a retaining pin 86. A posterior shock absorber 85 is retained in place between the snubber 42 and keel 52 by attaching a portion of the shock absorber to the snubber 42, and by attaching an opposite portion to the keel 52 by a pair of retaining pins 88, 90.

Advantageously, both of the shock absorbers may easily be removed and replaced simply by removing the retaining pins and by disconnecting the posterior shock absorber 85 from the snubber 42. Easy removal and replacement of the shock absorbers allows for quick and inexpensive maintenance of the prosthesis.

Operation of the prosthesis during ambulation or other physical exercise will now be described. Upon heel strike the heel arm 64 of the sole spring arm 54 abuts against the ground and is deflected upwards towards the keel 52. Deflection of the heel arm 64 causes the keel 52 to pivot about the axle 50 so that the posterior portion 76 of the keel 52 is driven towards the snubber 42 to compress the posterior shock absorber 85. If the amputee is undertaking more vigorous exercise (such as running for example) then the deflection of the sole spring arm heel portion 52 may cause it to abut the secondary spring arm heel portion 68 and to also deflect the secondary spring arm heel portion towards the keel 52.

As the amputee moves forward the prosthesis rolls over from the heel strike phase to the flat foot phase. Rolling over from the heel strike phase allows the sole spring arm heel portion 64 (and possibly also the secondary spring arm heel portion 68) to return to its undeflected state and the posterior shock absorber 85 to return to its non-compressed state. Relaxation of the sole spring arm heel portion 64 and the posterior shock absorber 85 returns energy that facilitates transition from the heel strike phase to the flat foot phase shown in FIG. 2, and during roll over to the toe-off phase.

The amputee's momentum and the energy returned from the heel strike phase causes the foot to roll over from the flat foot phase to the toe-off phase. As the foot rolls over to the toe-off phase, the toe arm 62 of the sole spring arm 54 abuts against the ground and is deflected upwards towards the keel 52. Deflection of the toe arm 62 causes the keel 52 to pivot about the axle 50 so that the anterior portion of the keel is driven towards the anterior portion of the snubber to compress the anterior shock absorber 82. Deflection of the toe arm 62 in the manner described also causes the posterior portion 76 of the keel 52 to be pivoted away from the snubber 42. Pivoting the keel 52 away from the snubber 42 causes the posterior shock absorber 85, which is connected to both the posterior portion 80 of the snubber 42 and the posterior portion 76 of the keel 52, to be placed under tension. If the amputee is undertaking more vigorous exercise (such as running for example) then the deflection of the sole spring arm toe portion 62 may cause it to abut the secondary spring arm toe portion 68 and to also deflect the secondary spring arm toe portion towards the keel 52.

When the amputee moves from the toe-off phase relaxation of the sole spring arm toe portion 62 (and possibly also the secondary spring arm toe portion 68) returns energy that facilitates movement from the toe-off phase of the amputee's gait. This energy return is further complemented by the relaxation of the anterior shock absorber 82 from its compressed state to its uncompressed state, and by the recovery of the energy stored therein. In addition, energy recovery is further improved by the relaxation of the posterior shock absorber 85 from its tensioned state to its untensioned state. It can be seen therefore that the prosthesis shown in FIG. 2 greatly increases the amount of energy that may be recovered during ambulation (and thus facilitates ambulation) when compared with previously proposed devices.

Figure 3:
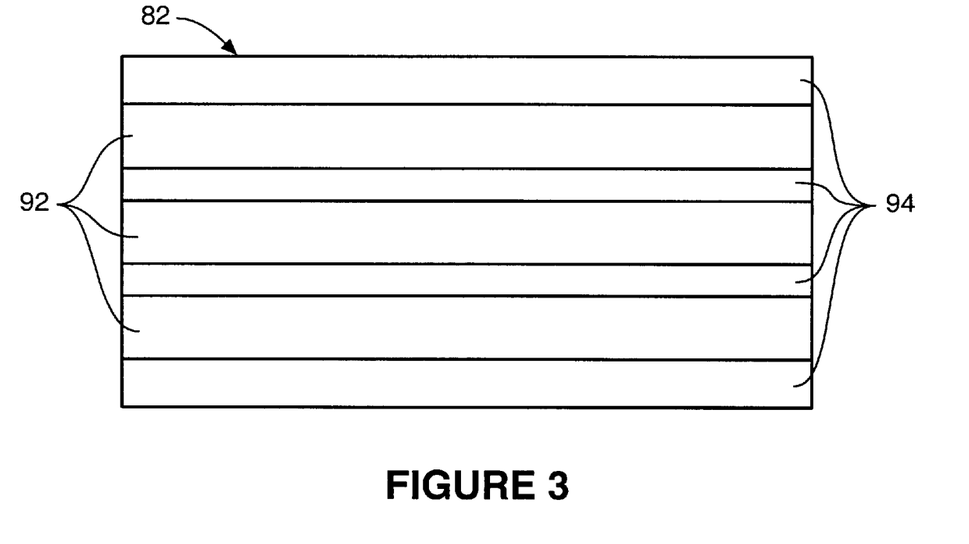
FIG. 3 is an elevation of an anterior shock absorber suitable for use with the foot of FIG. 2.

FIG. 3 is an elevation of an anterior shock absorber suitable for use with the foot of FIG. 2. As mentioned above, previously proposed shock absorbers have been prone to accelerated wear particularly when used by amputees of over 90 kg in weight. The shock absorbers shown in FIGS. 3 and 4 have been conceived to address these problems, and to further assist in energy recovery.

As shown in FIG. 3, the anterior shock absorber 82 is of a sandwich-type construction and comprises alternate layers of compressible material 92 (i.e. resiliently deformable material) and rigid or substantially non-compressible material 94 (such as a metallic or composite material). The compressible material 92 is employed as an energy storage device that aids energy recovery during ambulation. The rigid material 94 helps reduce the degree of deformation of the shock absorber 82 and thus reduce the wear of the shock absorber during ambulation. In the preferred embodiment the anterior shock absorber comprises a sandwich of differing layers arranged thus: rigid material (or substantially non-compressible material)/compressible material/rigid material/compressible material/rigid material.

Many different types of compressible material may be employed for the compressible layers 92. A presently preferred composition for the anterior shock absorber 82 compressible material provides a hardness of 65 IRHD and is available from Rapra Technology Limited, Shawbury, Shrewsbury, United Kingdom. The 65 IHRD composition comprises the ingredients set out below in Table 1.

Figure 4:
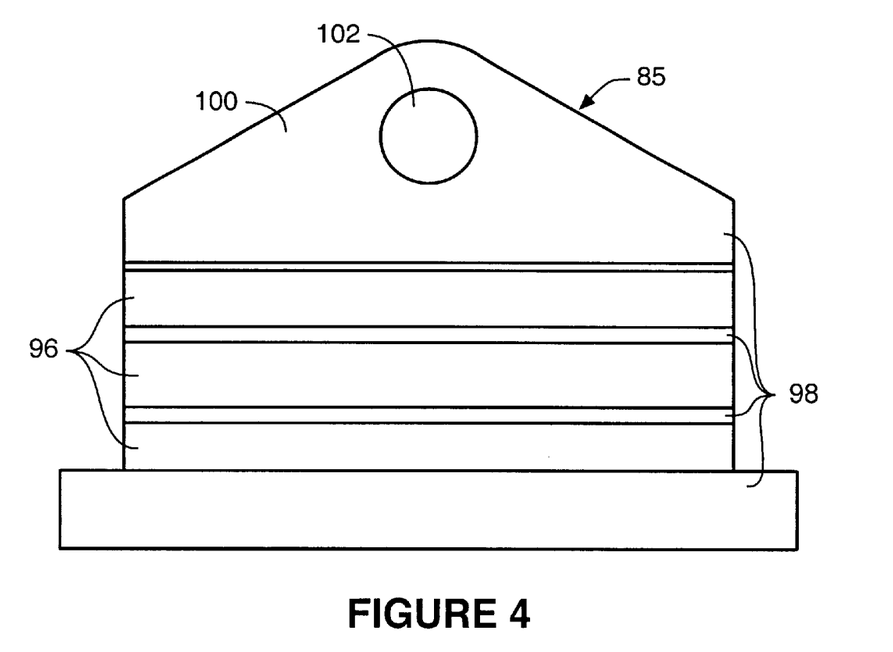
FIG. 4 is an elevation of a posterior shock absorber suitable for use with the foot of FIG. 2.

FIG. 4 is an elevation of a posterior shock absorber suitable for use with the foot of FIG. 2. The posterior shock absorber 85 is of similar construction to that of the anterior shock absorber and is preferably of a greater hardness in the order of 75 IRHD. As shown, the posterior shock absorber 85 comprises a sandwich of compressible layers 96 and rigid or substantially non-compressible layers 98. As with the anterior shock absorber 82, the compressible material 96 is employed as an energy storage device that aids energy recovery during ambulation. The rigid material 98 helps reduce the degree of deformation of the shock absorber 85 and thus reduce the wear of the shock absorber during ambulation. In the preferred embodiment the posterior shock absorber comprises a sandwich of differing layers arranged thus: rigid material (or substantially non-compressible material)/compressible material/rigid material/compressible material/rigid material/compressible material/rigid material. The secondarymost rigid material layer 100 is formed with a pair of roughly triangular sidearms that each have a bore 102 therethrough to allow the posterior shock absorber 85 to be connected to the snubber 42 as described above.

Once again, many different types of compressible material may be employed for the compressible layers 96. A presently preferred composition for the posterior shock absorber 85 compressible material provides a hardness of 75 IRHD and is available from Rapra Technology Limited, Shawbury, Shrewsbury, United Kingdom. The 75 IHRD composition comprises the ingredients set out below in Table 1.

The rigid or non-compressible layers 94, 98 are preferably of a metallic material and a variety of suitable metals, and alternative sufficiently rigid materials, will be apparent to those persons skilled in the art.

TABLE 1

| Ingredient | 65 IHRD Composition Part Hardness Rubber (phr) | 75 IHRD Composition |
|---|---|---|
| SMR CV 60 | 100.0 | 100.0 |
| HAF N330 | 60.0 | 80.0 |
| Circo Light Rubber Oil | 10.0 | 10.0 |
| Zinc Oxide | 10.0 | 10.0 |
| Stearic Acid | 2.0 | 2.0 |
| Flectol H | 2.0 | 2.0 |
| Santoflex 13 | 2.0 | 2.0 |
| Strucktol WB16 | — | 2.0 |
| Sulphur | 1.5 | 1.5 |
| CBS | 1.2 | 1.2 |
| IMTD | 0.2 | 0.2 |

Some or all of the materials listed in Table 1 may be TradeMarks (registered or otherwise) of Rapra Technology Limited or others and all rights are hereby acknowledged as belonging to their respective owners.

Figure 5:
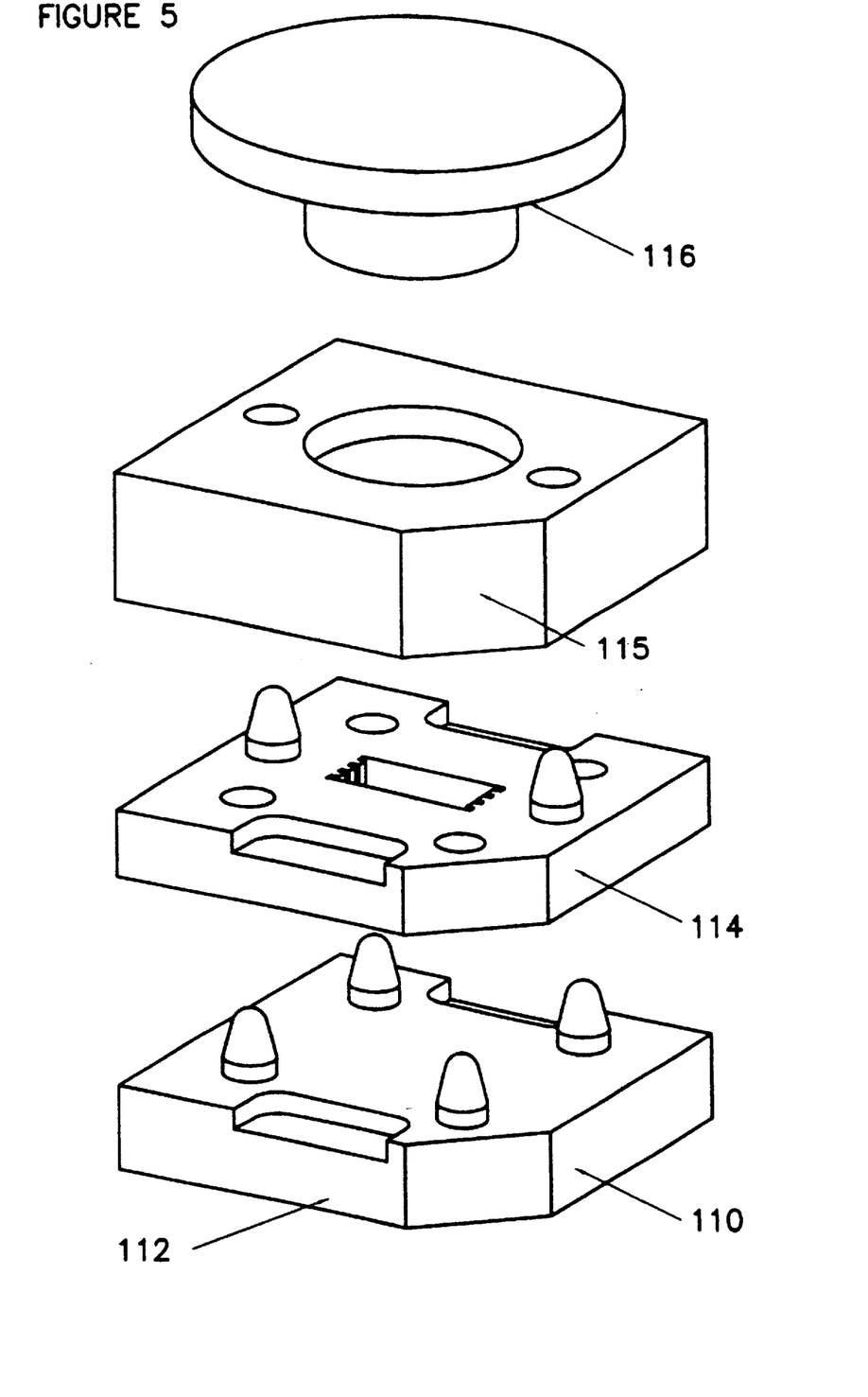
FIG. 5 is a schematic representation of a mechanism for forming the shock absorber of FIG. 3.
Figure 6:
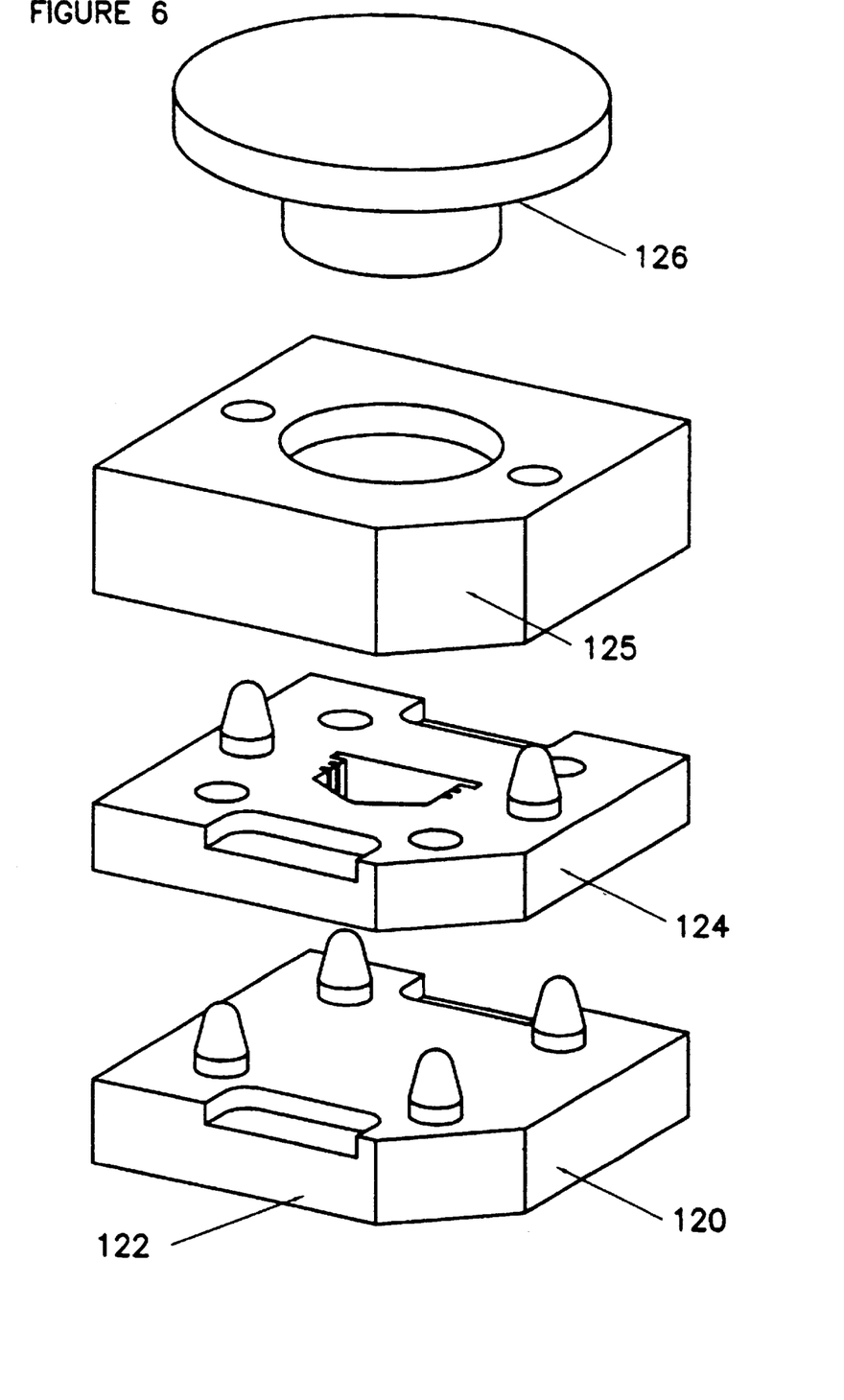
FIG. 6 is a schematic representation of a mechanism for forming the shock absorber of FIG. 4.

FIGS. 5 and 6 are schematic representations of mechanisms for forming the shock absorbers of FIGS. 3 and 4, respectively.

As shown, the shock absorbers 82, 85 are preferably formed by a moulding process. The moulds 110, 120 are each three-piece moulds comprising backing plates 112, 122, shaping plates 114, 124, top plates 115, 125 and plungers 116, 126. To fabricate the shock absorbers, the shaping plates 114, 124 are each secured to a corresponding backing plate 112, 122 and then layers of substantially non-compressible or rigid material are arranged at appropriate positions in the shaping plates 114, 124. The top plates 115, 125 are secured to the shapingplates and suitable molten compressible material is then driven into the shaping plates 114, 124 by means of respective plungers 116, 126. Once the compressible material has solidified the mould pieces can be removed to leave the finished shock absorber.

FIG. 7 is a cross-sectional view of a cosmesis that is suitable for use with the prosthesis of FIG. 2 or any other suitable prosthesis. The cosmesis 130 is of a suitable elastomeric material known to persons skilled in the art and is shaped to look like a foot. The cosmesis is hollow to accommodate the prosthesis and, in this embodiment, is provided with strengthening means to help alleviate problems caused by unwanted flexing of the cosmesis 130.

In addition to the various constructional problems outlined above, it is also important for the cosmesis 130, and indeed the foot as a whole, to behave as similarly to a normal human foot as possible in order to make the prosthesis less conspicuous for the amputee. For example, it has been noted that the cosmesis can flex across the front of the foot in the region of the toes during ambulation. This flexing provides an immediate indication to other persons that the foot is part of a prosthesis as it is wholly unnatural.

To help alleviate this problem it is proposed to provide strengthening means 132 in the sole of the cosmesis 130. The strengthening means provides extra resilience to flexing at the very point of the cosmesis where it is most needed, namely in the region of the toes. In this embodiment the strengthening means is formed within the sole, but it will of course be apparent that it could be formed in an upper portion of the cosmesis forming the front of the foot.

It is important that the strengthening means does not prevent flexing as this too would be unnatural, and thus the choice of material from which the strengthening means is made is important. Investigations have shown that a material known as Ferravel LX 36[1] is particularly suitable, but other suitable materials will be apparent to persons skilled in the art. By incorporating a strengthening means of a suitable material into the cosmesis in the manner described it is possible to reduce unnatural flexing of the cosmesis and thus to further improve the appearance of the prosthesis.

[1] Ferravel LX 36 is a TradeMark of Chamberlain Phipps Materials Limited of Wanlip Road, Syston, Leicester, United Kingdom.

As mentioned above, FIG. 8 is a schematic view of an endoskeletal artificial leg 200 which includes a prosthetic foot 40 such as that shown in FIG. 2. The leg comprises an internal skeleton which in this embodiment comprises a shin tube 210, a hinge 220 to simulate a knee and a thigh tube 240. The tubes may be of carbon fibre, titanium or of a variety of other materials. The lover end of the shin tube is provided with a socket 250 to which the connecting means 46 of the foot 40 may be connected, and the upper end of the thigh tube 240 is provided with a socket 260 by means of which the leg may be fixed to a patient. Packing 270 can be provided about the endoskeleton to simulate the bulk of a normal human leg.

Figure 9:
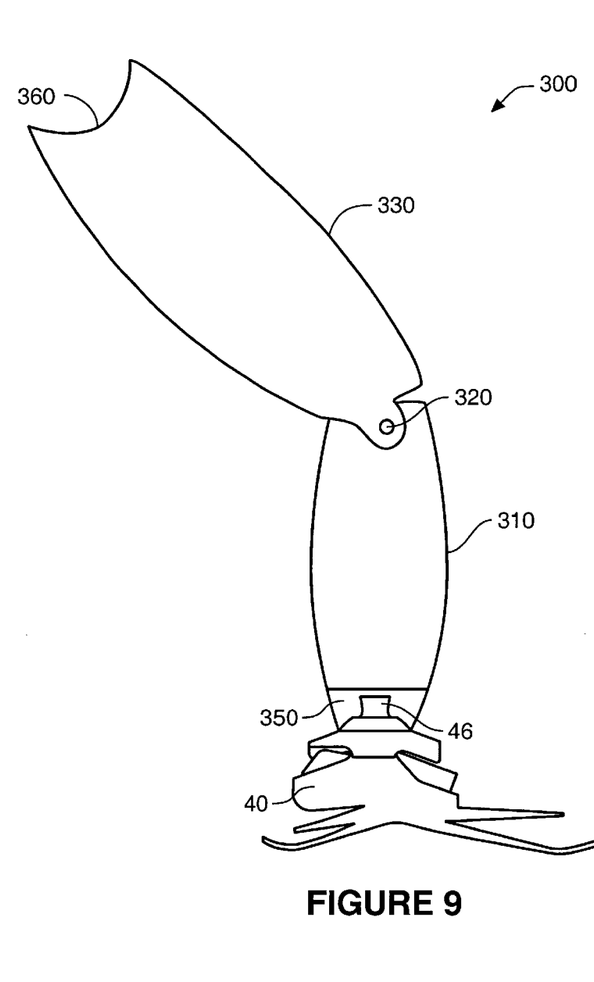
FIG. 9 is a schematic view of an exoskeletal artificial leg.

FIG. 9 is a schematic view of an exoskeletal artificial leg 300. The leg of this figure comprises a shin portion 310 hingedly attached by a hinge 320 to a thigh portion 330. A prosthetic foot 40 may be affixed to the shin portion 340 by engaging the connecting means 46 of the foot 40 with a socket 350 attached or comprising a part of the shin portion 310. The upper end of the thigh portion 330 is provided with a socket 360 by means of which the leg may be fixed to a patient.

It will be understood that illustrative embodiments of the invention have been described herein, and that modifications may be made thereto without departing from the scope of the invention.

For example, whilst the shock absorbers of the present embodiment are of a multi-layer construction, it will be appreciated that conventional shock absorbers may be provided instead. It is also possible for only one of the posterior or anterior shock absorbers to be of a multi-layer construction.

Figure 8:
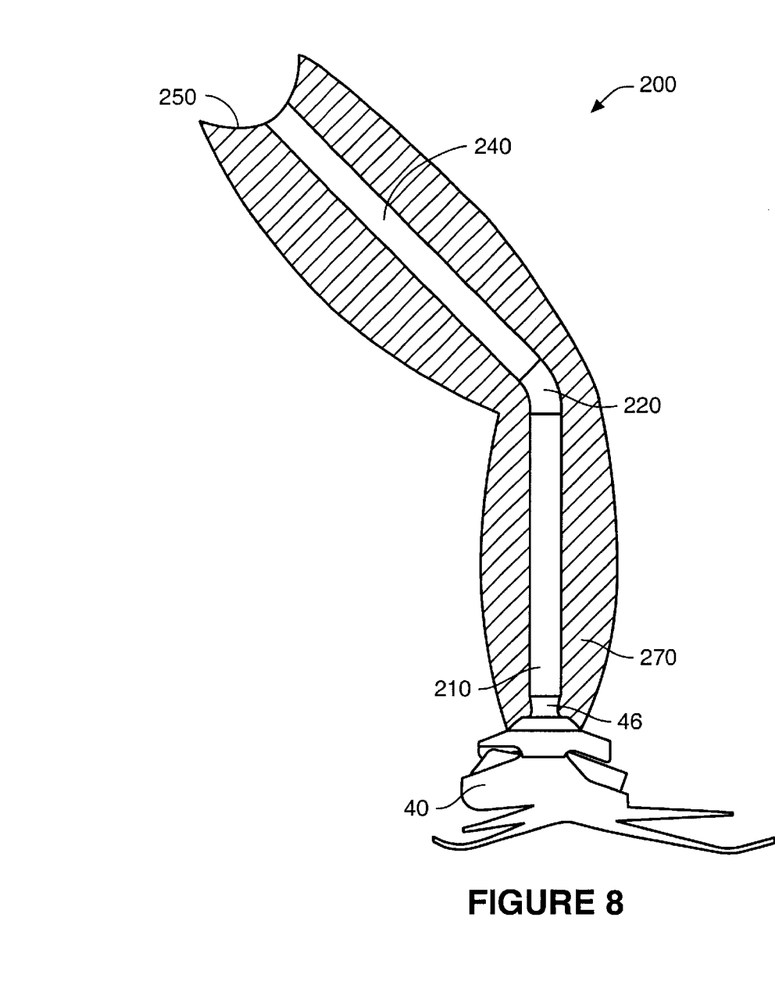
FIG. 8 is a schematic view of an endoskeletal artificial leg.

Similarly, whilst the legs shown in FIGS. 8 and 9 are designed to replace lost legs substantially in their entirety, it will be apparent that the leg may be adapted if the patient has only lost their leg below the knee, for example.

What is claimed is:

1. A prosthetic foot comprising:
   a spring assembly having an anterior component and a posterior component, the spring assembly including a secondary resiliently flexible member fixedly attached to a keel, and one or more resiliently flexible sole members attached to said secondary flexible member;
   a snubber pivotally connected to said keel for limiting movement of said spring assembly during ambulation; and
   anterior and posterior shock absorbers provided between respective components of said spring assembly and said snubber;
   wherein the arrangement of said posterior shock absorber, said spring assembly, and said snubber is such that ambulation results in the generation of a compressive force in said posterior shock absorber during a heel strike phase and a tensile force in said posterior shock absorber during a toe-off phase.

2. A prosthetic foot according to claim 1, wherein said anterior shock absorber is replaceable.

3. A prosthetic foot according to claim 1, wherein said posterior shock absorber is replaceable.

4. A prosthetic foot according to claim 1, wherein said posterior shock absorber is releasably attached to said spring assembly and said snubber.

5. A prosthetic foot according to claim 1, the resiliently flexible members each having a pair of cantilevered arms.

6. A prosthetic foot according to claim 5, wherein one of said flexible members is shorter than the other.

7. A prosthetic foot according to claim 5, wherein said flexible members are releasably attached to the keel.

8. A prosthetic foot according to claim 1, wherein at least one of said anterior and posterior shock absorbers are of a multi-layer construction.

9. A prosthetic foot according to claim 8, wherein at least one of said anterior and posterior shock absorbers are of a multi-layer construction comprising a sandwich of compressible and substantially non-compressible or rigid layers.

10. A prosthetic foot according to claim 1, wherein said posterior shock absorber is less compressible than said anterior shock absorber.

11. A prosthetic foot according to claim 1 with the anterior and posterior shock absorbers having a multi-layer construction with a sandwich of deformable layers and substantially non-deformable layers, the hardness of the anterior shock absorber being less than 70 IHRD and the hardness of the posterior shock absorber being less than 80 IHRD.

12. A prosthetic leg comprising an exoskeleton and a prosthetic foot according to any of claim 1.

13. A prosthetic leg comprising an endoskeleton and a prosthetic foot according to any of claim 1.

* * * * *